United States Patent [19]

Stanworth et al.

[11] Patent Number: 5,945,104
[45] Date of Patent: Aug. 31, 1999

[54] PEPTIDES FOR ANTI-ALLERGY TREATMENT

[75] Inventors: Denis Raymond Stanworth, Birmingham; Ian Victor Lewin, Tamworth, both of United Kingdom

[73] Assignee: Peptide Therapeutics Limited, Cambridge, United Kingdom

[21] Appl. No.: 08/817,933

[22] PCT Filed: Nov. 3, 1995

[86] PCT No.: PCT/GB95/02580

§ 371 Date: Jun. 27, 1997

§ 102(e) Date: Jun. 27, 1997

[87] PCT Pub. No.: WO96/14333

PCT Pub. Date: May 17, 1996

[30] Foreign Application Priority Data

Nov. 4, 1994 [GB] United Kingdom .................... 9422294

[51] Int. Cl.⁶ ......................... A61K 39/385; A61K 39/00; A61K 38/03; C07K 1/00
[52] U.S. Cl. ..................... 424/184.1; 424/185.1; 424/193.1; 530/327; 530/328; 530/329; 530/330; 530/403
[58] Field of Search ................ 530/391.1, 403, 530/868, 327, 328, 329, 330; 424/178.1, 182.1, 193.1, 184.1, 185.1

[56] References Cited

FOREIGN PATENT DOCUMENTS

| | | |
|---|---|---|
| 0 000 252 | 1/1979 | European Pat. Off. . |
| 0 288 965 | 11/1988 | European Pat. Off. . |
| 0 343 460 | 11/1989 | European Pat. Off. . |
| 0 403 312 | 12/1990 | European Pat. Off. . |
| 0 427 347 | 5/1991 | European Pat. Off. . |
| 0 517 589 | 12/1992 | European Pat. Off. . |
| 0 592 230 | 4/1994 | European Pat. Off. . |
| 86 07263 | 12/1986 | WIPO . |
| 0 378 881 | 7/1990 | WIPO . |
| 90/15878 | 12/1990 | WIPO . |
| 94 18345 | 8/1994 | WIPO . |
| 95 10532 | 4/1995 | WIPO . |

OTHER PUBLICATIONS

Ra, Tomoyasu et al. "Polypeptides of monoclonal antibody to human . . . " Chemical Abstracts, vol. 123, No. 15, Oct. 9, 1995, abstract No. 196596.

Oka, et al. "Preparation of peptides and . . . " CA 122,5, 56588 (1995).

Ramage et al, J. Chem. Soc. Perkin Trans I. "Application of Diphenylphosphonic . . . ," 1985 (3), pp. 461–470.

Nio et al., FEBS Letters 1992, 314 (3), pp. 229–231. "Inhibition of passive cutaneous anaphylaxix . . . ".

*Primary Examiner*—David Saunders
*Assistant Examiner*—F. Pierre VanderVegt
*Attorney, Agent, or Firm*—Nixon & Vanderhye

[57] ABSTRACT

Peptides of the above-mentioned sequence wherein Xaa is any amino acid residue, but most preferably Val or Ile, and their simple derivatives, including those chain-extended at the N-terminus or C-terminus, are useful in anti-allergy treatment.

11 Claims, No Drawings

PEPTIDES FOR ANTI-ALLERGY TREATMENT

BACKGROUND OF THE INVENTION

1. Field of the Invention

This invention relates to peptides, believed novel per se and to their use in a vaccine against allergies.

Amino acids and amino acid residues are represented herein by their standard codes as identified by the IUPAC-IUB Biochemical Nomenclature Commission and represent D and L amino acids, their analogues or derivatives.

2. Description of the Related Art

PCT Application Publication No. WO90/15878 describes certain peptides, conjugated or otherwise rendered non-self, useful in anti-allergy treatment. These peptides are derived from or analogous to a sequence of human IgE known to represent an active site implicated in histamine release. It was found that they are effective immunogens, without causing substantial release of histamine.

The structural requirements of these peptides are a cationic N-terminal head, e.g. of the sequence Lys Thr Lys and a hydrophobic C-terminal tail, e.g. of the sequence:

```
Phe Phe Val Phe          (SEQ ID NO: 1)
 1
``` as in the decapeptide:

```
                              (SEQ ID NO: 2)
Lys Thr Lys Gly Ser Gly Phe Phe Val Phe
 1           5               10
```

It is a problem to extend the range of peptides useful for an anti-allergy vaccine.

SUMMARY OF THE INVENTION

It has now surprisingly been found that peptides of the sequence:

```
Phe Phe Xaa Phe          (SEQ ID NO: 3)
 1
``` where Xaa is any amino acid residue afford some protection against challenge by allergens. Such peptides and their C-terminal and or N-terminal derivatives constitute a first aspect of the invention.

In a second aspect, the invention provides conjugates of the peptides with a carrier. As used here a carrier means a moiety capable of stimulating T cell help in order to activate production of antibodies by B cells.

Thirdly, the invention includes a pharmaceutical composition comprising a peptide or conjugate of the invention, together with an adjuvant.

Fourthly, the invention includes the peptides and conjugates for use in the treatment of allergies. In particular it includes their use in the manufacture of a formulation for use as an anti-allergy vaccine where national law permits, it further includes a method of treating a patient suffering from or susceptible to an allergy which comprises administering to the patient an amount of a said peptide, preferably in the form of a conjugate, effective to combat the allergy.

The term "N-terminal derivatives thereof" is used herein to include peptides having N-terminal blocking or inactivating groups, e.g. acetyl groups as well as N-terminal short-chain amino acid or peptide "handles", of 1 to 4 amino acids in length, especially neutral residues, e.g. Gly-Ser-Gly as in the above-mentioned decapeptide or Arg or Lys. Such handle residues can themselves be N-terminally blocked.

The term "C-terminal derivatives thereof" includes amides and short-chain amino acid or peptide "tails", of 1 to 4 amino acids in length, especially of neutral residues, which may themselves be C-amidated. Other inactivating groups can be used in place of amides.

Other aspects of the invention are set out in the attached claims.

DESCRIPTION OF THE PREFERRED EMBODIMENTS

Peptides according to the present invention comprise the sequence:

```
Phe Phe Xaa Phe                          (SEQ ID NO:3)
```

Xaa can be any amino acid residue, but is preferably not a neutral hydrophobic residue other than Val or Ile.

More preferably Xaa is selected from Val, Ile, Asp, Gly, Lys, Arg and His. Most preferably Xaa is Val or Ile.

The peptides of the invention can be synthesised by methods well known in the art such as the "F-moc" method.

To conjugate the simple peptides, any of the methods of coupling and carrier proteins disclosed in the prior PCT application can be used.

The carrier can itself be a peptide of from typically 9–30 amino acids. In this instance the carrier and the peptides of the invention can be synthesised together as a single entity.

The conjugates can contain more than one residue of a peptide of the invention, as, for example, in branched peptides having the above-recited sequence SEQ ID NO: 3 present on arms of a branched core, e.g. of polylysine, see. e.g. J. P. Tam, Proc. Natl. Acad. Sci. USA 85, 5409–5413 (1988).

The peptides can be extended at either end by "handles" or "tails" as mentioned above. These are conveniently of neutral residues, these being thought unlikely, to interfere with the hydrophobic sequence (SEQ ID NO: 3). Alternatively, a single arginine or lysine residue at the N-terminus can be tolerated.

The vaccine compositions and methods of active immunization can be as described in the prior PCT application. Both prophylactic and therapeutic uses are envisaged for such a vaccine.

The invention will now be described with reference to the following illustrative examples:

EXAMPLE 1

Three short C-amidated peptides were synthesized, by the F.moc procedure, two of these incorporating an extra (glycine) residue at their C-termini (for technical reasons), viz:

F92 Gly Ser Gly Phe Phe Gly NH$_2$ (C-amide of SEQ ID NO: 4)

F93 Phe Phe Val Phe Gly-NH$_2$ (C-amide of SEQ ID NO: 5)

F94 Lys Thr Lys Gly Ser-NH$_2$ (C-amide of SEQ ID NO: 6)

The level of anti-allergy protection induced in rats by immunization with the peptides was determined.

The peptides were conjugated to PPD (purified protein derivative of tuberculin) by adding 3 mg of peptide in 1 ml water to 5 mg of PPD in 1 ml water. 1 ml of glutaraldehyde (21 mM) was then added slowly dropwise over a period of 10 minutes with gentle mixing. The mixture was then left at 4° C. for 2 hr with gentle mixing. The conjugate was then dialyzed against several changes of phosphate buffered saline (pH 7.2) and the volume adjusted to give a peptide concentration of 1 mg/ml.

All peptides were prepared for use by vortexing 2 parts of peptide conjugate with 1 part Al(OH)$_3$ and incubating at 20° C. for 30 minutes; this procedure was used in all subsequent injections.

Six Wistar rats were injected subcutaneously with 0.2 ml of the above mixture on days 0, 14 and 28. On day 28, three rats were also sensitized by injection (subcutaneous) of ovalbumin-β-pertussis mixture in the standard manner.

These three groups of three rats were subsequently challenged with allergen on day 49, by intravenous injection of ovalbumin (5 mg) and cardiac bleeds taken, for histamine assay.

Results (following challenge with ovalbumin):

| Immunizing Peptide | Rat No. | Histamine released (ng/ml) Pre-challenge | Post-challenge | Cyanosis Score |
|---|---|---|---|---|
| F92 | 1 | 288 | 7,232 | 2 |
|  | 2 | 320 | 5,280 | 2 |
|  | 3 | 288 | 832 | 5 |
|  | Mean | 299 | 4,448 | 3 |
| F93 | 1 | 224 | 1,200 | 0 |
|  | 2 | 288 | 1,136 | 3 |
|  | 3 | 256 | 704 | 2 |
|  | Mean | 256 | 1,103 | 1.7 |
| F94 | 1 | 256 | 2,432 | 3 |
|  | 2 | 480 | 3,488 | 2 |
|  | 3 | 448 | 10,244 | 3 |
|  | Mean | 395 | 5,388 | 2.7 |

Cyanosis was scored by examining the color of the rats' ears after ovalbumin injection and grading on a 0–5 scale wherein: 0=pink and 5=dark purple. A low number indicates efficacy. The peptide of the invention (F93) gave markedly better results than the other two.

EXAMPLE 2

Conjugates of peptides having the general formula Gly Phe Phe Xaa Phe-NH$_2$ (SEQ ID NO:10) were prepared. Gly was incorporated merely as a spacer to facilitate attachment of the peptide to the carrier protein keyhole limpet haemocyanin during production of the peptide using the F. moc procedure. 20 peptides were prepared corresponding to each possible substitution of Xaa with a naturally occurring amino acid residue. Rather than testing individual conjugates in individual animals the peptides were pooled and antibodies were raised against each pool in rats. Membership of a pool was determined by the comparative physicochemical properties of each peptide. The pools were as follows: i) hydrophobic, ii) neutral, iii) acidic, and iv) basic.

Male Wistar rats were immunized with an individual pool and serum was taken from the rats six and eight weeks thereafter. The serum was tested for anti-(Lys Thr Lys Gly Ser Gly Phe Phe Val Phe-NH$_2$) IgG(Fc) antibodies (anti-C amidated SEQ ID NO:2 antibodies). High levels of production of these antibodies indicated that the respective pool included at least one peptide which is an effective immunogen and this peptide could be useful for an anti-allergy vaccine.

Results: (Background O.D. (n=10)=0.244, determined with pre-immune sera)

| Peptide GFFXF Substitution | 6 weeks 1:4 Mean O.D. (n = 2) | Standard Error | 8 Weeks 1:4 Mean O.D. (n = 2) | Standard Error |
|---|---|---|---|---|
| Hydrophobic W | 0.572 | 0.268 | 0.599 | 0.245 |
| Hydrophobic V | 1.551 | 0.015 | 1.601 | 0.025 |
| Acidic (pooled) D,E | 0.987 | 0.491 | 1.314 | 0.126 |
| Basic (pooled) K,R,H | 1.472 | 0.019 | 1.358 | 0.009 |
| Neutral (pooled) S,T,Y,N,Q,C,G | 1.039 | 0.109 | 0.995 | 0.134 |
| Hydrophobic (pooled) A,L,I,P,F,M | 1.127 | 0.209 | 0.89 | 0.029 |

It is evident from the above table of results that each pool (including the acidic and basic pools of negatively and positively charged amino-acids respetively) was capable of eliciting antibodies against C amidated SEQ ID NO:2. This is surprising since Val, which is an uncharged hydrophobic amino acid residue, is found in SEQ ID No. 2.

The following claims define some important aspects of the invention, but do not purport to include every conceivable aspect for which protection might be sought and should not be construed as detracting from the generality of the inventive concepts hereinbefore described.

We claim:

1. Immunogenic conjugates of peptides of the general formula Phe Phe Xaa Phe (SEQ ID NO:3) wherein Xaa is any amino acid residue, or an N-terminal and/or C-terminal derivative thereof which has up to 4 additional amino acid residues at each terminus and is linked to a carrier, wherein the derivative is further a terminally blocked or inactivated peptide, and the carrier is a moiety capable of stimulating T cell help in order to activate production of antibodies by B Cells.

2. Immunogenic conjugates of peptides of the general formula Phe Phe Xaa Phe (SEQ ID NO:3) wherein Xaa is any amino acid residue or an N-terminal and/or C-terminal derivative thereof which has up to 4 additional amino acid residues at each terminus and is linked to a carrier, wherein any one but only one of the Phe residues is replaced by a Trp or Tyr, and the carrier is a moiety capable of stimulating T cell help in order to activate production of antibodies by B Cells.

3. Conjugates according to claim 1 wherein Xaa is selected from the group consisting of amino acid residues Val, Ile, Asp, Glu, Lys, Arg and His.

4. Conjugates according to claim 1 where Xaa is selected from the group consisting of amino acid residues Val and Ile.

5. Conjugates according to claim 1 wherein the additional amino acid(s) are either neutral residue(s) or a single N-terminal arginine or lysine residue.

6. Conjugates according to claim 1 wherein the carrier is a protein or wherein two or more residues of a peptide according to claim 1 are linked to a branched core.

7. A pharmaceutical composition comprising a conjugate claimed in claim 1, together with an adjuvant.

8. A method of treating a patient suffering from or susceptible to an allergy which comprises administering to the patient an amount of a conjugate according to claim 1, effective to combat the allergy.

9. A process for synthesizing a conjugate according to claim 1 which comprises synthetically preparing a peptide by combining amino acids in the sequence shown in SEQ ID NO:3; and covalently binding a carrier to the peptide.

10. Conjugates according to claim 1 wherein the carrier is KLH, tetanus-toxoid or PPD.

11. Conjugates according to claim 1 wherein the carrier is selected from the group consisting of:

i) Glu Lys Lys Ile Ala Lys Met Glu Lys Ala Ser Ser Val Phe Asn Val (SEQ ID NO:7);

ii) Phe Asn Asn Phe Thr Val Ser Phe Val Val Leu Arg Val Pro Lys Val Ser Ala Ser His Leu Glu (SEQ ID NO:8); and iii) Gln Tyr Ile Lys Ala Asn Ser Lys Phe Ile Gly Ile Thr Glu (SEQ ID NO:9).

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (v) FRAGMENT TYPE: linear (xi) SEQUENCE DESCRIPTION: SEQ ID NO:1:

```
Phe Phe Val Phe
1

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:2:

Lys Thr Lys Gly Ser Gly Phe Phe Val Phe
1               5                   10

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (v) FRAGMENT TYPE: linear (xi) SEQUENCE DESCRIPTION: SEQ ID NO:3:

Phe Phe Xaa Phe
1

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gly Ser Gly Phe Phe Gly
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Phe Phe Val Phe Gly
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:6:

Lys Thr Lys Gly Ser
1               5

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Glu Lys Lys Ile Ala Lys Met Glu Lys Ala Ser Ser Val Phe Asn Val
1               5                   10                  15

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Phe Asn Asn Phe Thr Val Ser Phe Val Val Leu Arg Val Pro Lys Val
1               5                   10                  15

Ser Ala Ser His Leu Glu
            20

(2) INFORMATION FOR SEQ ID NO:9:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gln Tyr Ile Lys Ala Asn Ser Lys Phe Ile Gly Ile Thr Glu
1               5                   10

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Phe Phe Xaa Phe
1               5